(12) United States Patent
Gupta

(10) Patent No.: US 9,374,954 B2
(45) Date of Patent: Jun. 28, 2016

(54) METHODS OF INITIATING PLANT SOMATIC EMBRYOS

(71) Applicant: WEYERHAESUER NR COMPANY, Federal Way, WA (US)

(72) Inventor: Pramod K. Gupta, Federal Way, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 283 days.

(21) Appl. No.: 14/104,075

(22) Filed: Dec. 12, 2013

(65) Prior Publication Data

US 2014/0178999 A1    Jun. 26, 2014

Related U.S. Application Data

(60) Provisional application No. 61/739,927, filed on Dec. 20, 2012.

(51) Int. Cl.
*A01H 4/00* (2006.01)
*C12N 5/00* (2006.01)

(52) U.S. Cl.
CPC . *A01H 4/005* (2013.01); *C12N 5/00* (2013.01)

(58) Field of Classification Search
None
See application file for complete search history.

(56) References Cited

U.S. PATENT DOCUMENTS

| | | | |
|---|---|---|---|
| 4,957,866 A | 9/1990 | Gupta et al. | |
| 5,034,326 A | 7/1991 | Pullman et al. | |
| 5,036,007 A | 7/1991 | Gupta et al. | |
| 5,041,382 A | 8/1991 | Gupta et al. | |
| 5,236,841 A | 8/1993 | Gutpa et al. | |
| 5,294,549 A | 3/1994 | Pullman et al. | |
| 5,482,857 A | 1/1996 | Gupta et al. | |
| 5,563,061 A | 10/1996 | Gupta et al. | |
| 5,564,224 A | 10/1996 | Carlson et al. | |
| 5,565,355 A * | 10/1996 | Smith | A01H 4/005 435/422 |
| 5,687,504 A | 11/1997 | Carlson et al. | |
| 5,701,699 A | 12/1997 | Carlson et al. | |
| 5,821,126 A | 10/1998 | Durzan et al. | |
| 5,856,191 A * | 1/1999 | Handley, III | A01H 4/001 435/420 |
| 6,119,395 A | 9/2000 | Hartle et al. | |
| 7,598,073 B2 | 10/2009 | Gupta et al. | |
| 8,012,753 B2 | 9/2011 | Gupta et al. | |
| 2005/0198713 A1 | 9/2005 | Gupta et al. | |

OTHER PUBLICATIONS

Klimaszewska, Plantlet development from immature zygotic embryos of hybrid larch through somatic embryogenesis, Plant Science, 63 (1989) 95-103.*

* cited by examiner

*Primary Examiner* — June Hwu
(74) *Attorney, Agent, or Firm* — Perkins Coie LLP

(57) ABSTRACT

Methods of initiating plant somatic embryos from megagametophytes are provided.

14 Claims, 1 Drawing Sheet

METHODS OF INITIATING PLANT SOMATIC EMBRYOS

CROSS-REFERENCE TO RELATED APPLICATION

This application is entitled to and claims the benefit of priority under 35 U.S.C. §119 from U.S. Provisional Application Ser. No. 61/739,927 filed Dec. 20, 2012, and titled "Protecting Your Invention Outside the United States," the contents of which are incorporated herein by reference.

BACKGROUND

Modern silviculture often requires the planting of large numbers of genetically identical plants that have been selected to have advantageous properties. Production of new plants by sexual reproduction, which yields botanic seeds, is usually not feasible. Asexual propagation, via the culturing of somatic or zygotic embryos, has been shown for some species to yield large numbers of genetically identical embryos, each having the capacity to develop into a normal plant.

Somatic cloning is the process of creating genetically identical plants from plant tissue other than male and female gametes. In one approach to somatic cloning, plant tissue is cultured in an initiation medium that includes hormones, such as auxins and/or cytokinins, to initiate formation of embryogenic tissue, such as an embryogenic suspensor mass, that is capable of developing into somatic embryos. Embryogenic suspensor mass, or ESM, has the appearance of a whitish translucent mucilaginous mass and contains early stage embryos. The embryogenic suspensor mass is further cultured in a multiplication medium that promotes multiplication and mass production of the embryogenic suspensor mass. The embryogenic suspensor mass is then cultured in a development medium that promotes development and maturation of cotyledonary somatic embryos that can, for example, be placed on germination medium to produce germinants, and subsequently transferred to soil for further growth, or alternatively, placed within manufactured seeds and sown in soil where they germinate to yield seedlings. Manufactured seeds are described, for example, in U.S. Pat. Nos. 5,564,224; 5,687,504; 5,701,699; and 6,119,395.

A continuing problem with somatic cloning of conifer embryos is stimulating efficient and cost-effective formation of somatic embryos that are capable of germinating to yield plants. Preferably, conifer somatic embryos, formed in vitro, are physically and physiologically similar, or identical, to conifer zygotic embryos formed in vivo in conifer seeds. There is, therefore, a continuing need for methods for producing viable conifer somatic embryos from conifer embryogenic cells.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect the present disclosure provides methods of initiating plant somatic embryos from a megagametophyte. The methods disclosed each include the steps of (a) dissecting a megagametophyte into a plurality of parts; and (b) culturing one or more of the plurality of parts of the dissected megagametophyte to initiate the formation of embryogenic suspensor mass.

In some embodiments, the methods of the present disclosure further include the steps of multiplying the embryogenic suspensor mass; culturing the embryogenic suspensor mass to produce cotyledonary embryos; and culturing the cotyledonary embryos to produce germinants.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
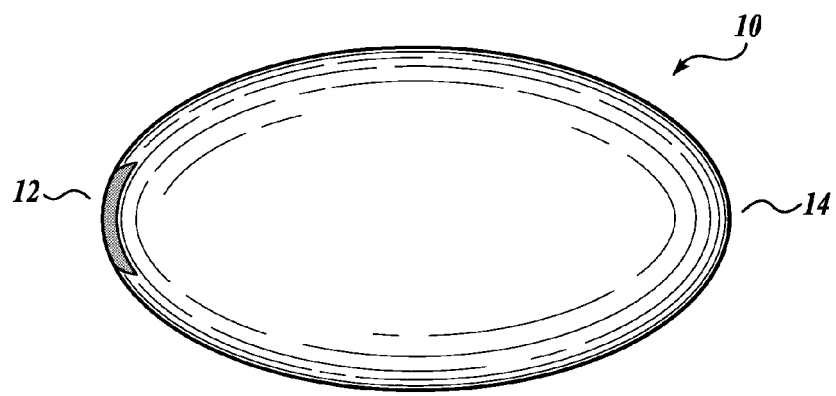
FIGS. 1A-1C are schematic diagrams illustrating dissection of a megagametophyte according to the methods of the present disclosure.

Unless specifically defined herein, all terms used herein have the same meaning as they would to one skilled in the art of the present disclosure.

As used herein, the term "embryogenic suspensor mass" (ESM) refers to early stage embryos in the process of multiplication by budding and cleavage.

As used herein, the term "embryogenic tissue" refers to an aggregate of tens to hundreds of embryogenic cells that form an embryogenic suspensor mass.

As used herein, the term "plant embryo" refers to either a zygotic plant embryo or a somatic plant embryo. A zygotic plant embryo is an embryo found inside a botanic seed produced by sexual reproduction. Somatic plant embryos can be produced by culturing embryogenic tissue by standard methods under laboratory conditions in which the cells comprising the tissue are separated from one another and urged to develop into minute complete embryos. As used herein, "plant embryo" includes embryos at various stages of development and includes both early-stage and cotyledonary embryos.

As used herein, the term "megagametophyte" refers to a female gametophyte produced by the megaspores of a plant.

As used herein, the term "micropyle" refers to a small opening at the end of the megagametophyte.

The somatic embryogenesis process is a process to develop plant embryos in vitro. Methods for producing plant somatic embryos are known in the art and have been previously described (see, e.g., U.S. Pat. Nos. 4,957,866; 5,034,326; 5,036,007; 5,041,382; 5,236,841; 5,294,549; 5,482,857; 5,563,061; and 5,821,126). Generally, the somatic embryogenesis process includes the steps of (1) initiation or induction, to initiate formation of embryogenic tissue, such as embryogenic suspensor mass (ESM), which is a white mucilaginous mass that includes early stage embryos having a long, thin-walled suspensor associated with a small head with dense cytoplasm and large nuclei; (2) multiplication, sometimes referred to as maintenance, to establish and multiply embryogenic tissue to form pre-cotyledonary embryos, which can be characterized as having smooth embryogenic heads, with multiple suspensors; (3) development, to develop and form mature cotyledonary somatic embryos; and (4) post development steps such as singulation, stratification, germination, placement into manufactured seeds, and transferring to soil for further growth and development.

The present disclosure is directed to the initiation step of the somatic embryogenesis process. In nature, following fertilization, a single zygote will naturally cleave to form multiple early-stage embryos. This process is referred to as "cleavage polyembryony." Typically a dominant embryo will emerge, and the others atrophy or do not develop due to limited resources within a seed. This natural process of cleavage polyembryony can be utilized in somatic embryogenesis to initiate the formation of embryogenic suspensor mass, which contains multiple early stage embryos.

In methods known in the art, whole megagametophytes are cultured on initiation medium. Numerous embryos that are naturally created in the megagametophyte due to cleavage polyembryony extrude out of the megagametophyte onto the medium. The extruded embryos continue to cleave and multiply on the medium to form embryogenic suspensor mass over a period of about 6-12 weeks. This process is described for example in Pullman et al., *Plant Cell Report* 22:22-26 (2003), and Durzan and Gupta, *Advances in Biotechnological Processes* 9:53-81 (1998).

Applicants have discovered that dissecting a megagametophyte before a dominant embryo has formed and culturing the dissected megagametophyte on initiation medium provides multiple embryos within the megagametophyte access to initiation medium and increases the chance of successful initiation of ESM from the megagametophyte. The methods of the present disclosure result in a significant increase in the percentage of megagametophytes forming embryogenic suspensor mass compared to the percentage of megagametophytes forming embryogenic suspensor mass using known methods of culturing whole, intact, megagametophytes.

In one aspect the present disclosure provides a plurality of methods for initiating plant somatic embryos from a megagametophyte. The methods of this aspect of the disclosure each include the steps of (a) dissecting a megagametophyte into a plurality of parts; and (b) culturing one or more of the plurality of parts of the dissected megagametophyte to initiate the formation of embryogenic suspensor mass. In one embodiment, the megagametophyte is dissected into two parts.

Figure 1B:
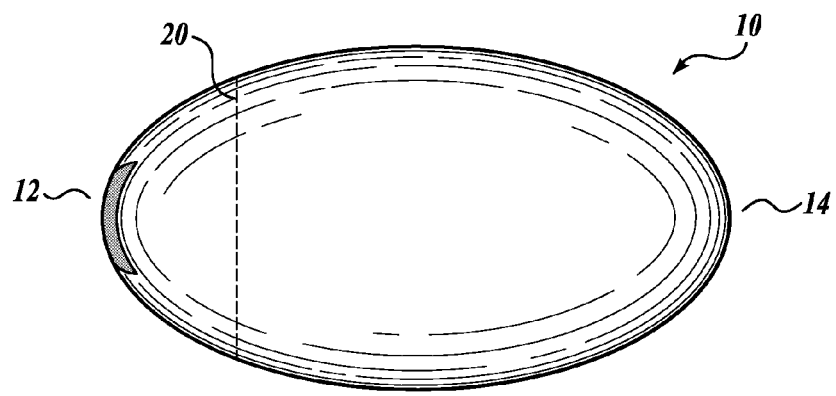
Figure 1C:
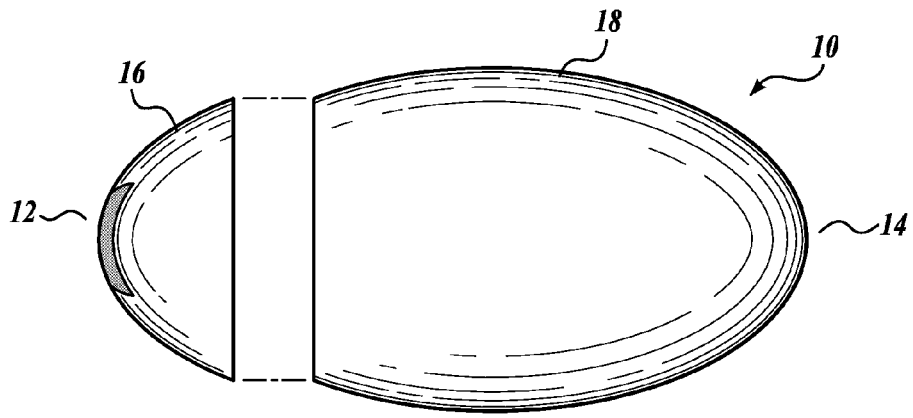

An example of dissection of a megagametophyte according to the methods of the present disclosure is illustrated in FIGS. 1A-1C. Referring to FIG. 1A, a megagametophyte 10 has a micropylar end 12. Embryos in various stages of cleavage are located at the end 14 of the megagametophyte 10 opposite and distal from the micropylar end 12. Referring to FIG. 1B, a megagametophyte 10 is dissected at a position 20 that is located proximal to the micropylar end 12. FIG. 1C illustrates a megagametophyte dissected into two parts 16 and 18.

In one embodiment, a megagametophyte 10 is dissected transversally to the longitudinal axis at a position 20 that is located from about one-eighth to about one-half of the length of the megagametophyte 10 and proximal to the micropylar end 12. In some embodiments the megagametophyte is dissected at a position that is located at any position within the range of about one-eighth of the length of the megagametophyte to about one-half of the length of the megagametophyte, such as ⅛, 3/16, ¼, 5/16, 6/16, 7/16, and ½. In some embodiments, a megagametophtye can be dissected at a position that is located more than one-half of the length of the megagametophyte, as measured from the micropylar end, provided the developing embryos within the megagametophyte are not damaged by the dissection.

In one embodiment, a megagametophyte 10 is dissected transversally to the longitudinal axis at a position 20 that is located at about one-eighth of the length of the megagametophyte 10 and proximal to the micropylar end 12. In one embodiment, a megagametophyte 10 is dissected transversally to the longitudinal axis at a position 20 that is located at about one-fourth of the length of the megagametophyte 10 and proximal to the micropylar end 12. In one embodiment, a megagametophyte 10 is dissected transversally to the longitudinal axis at a position 20 that is located at about one-half of the length of the megagametophyte 10 and proximal to the micropylar end 12.

In one embodiment, a megagametophyte is dissected before a dominant embryo has formed in the megagametophyte.

In one embodiment, the one or more parts of the dissected megagametophyte are cultured on initiation medium for a period of time sufficient to form embryogenic suspensor mass. Typically, the ESM are cultured on initiation medium at 25° C.±2° C. in the dark. In one embodiment, the one or more parts of the dissected megagametophyte are cultured on initiation medium for a period about three to twelve weeks to form embryogenic suspensor mass. In one embodiment, the one or more parts of the dissected megagametophyte are cultured on initiation medium for a period of about three to four weeks to form embryogenic suspensor mass.

The initiation medium generally includes inorganic salts and organic nutrient materials. For example, the initiation medium may include maltose as a carbohydrate source. Examples of useful maltose concentrations are within the range from about 1% to about 5%, such as about 1.5%. The osmolality of the initiation medium is typically about 160 mM/kg or even lower, but it may be as high as 170 mM/kg. The initiation medium typically includes growth hormones. Examples of hormones that can be included in the initiation medium are auxins (e.g., 2,4-dichlorophenoxyacetic acid (2,4-D), and naphthalene acetic acid) and cytokinins (e.g., 6-benzylaminopurine (BAP)). An exemplary initiation medium suitable for use in the methods of the present disclosure is provided in Table 2, although other initiation medium may be used.

In some embodiments the methods of the present disclosure further comprise transferring the ESM from the initiation medium to a series of medium to multiply and mass produce the ESM. In some embodiments the methods of the present disclosure further comprise transferring the multiplied ESM to development medium and culturing the ESM on development medium to form cotyledonary embryos. Suitable compositions of maintenance, multiplication, and development media for use in the somatic embryogenesis process are well-known in the art (see, e.g., U.S. Pat. No. 7,598,073).

After the development period, the cotyledonary somatic embryos can optionally be transferred to a maturation medium, and then subjected to post development steps such as singulation, stratification, germination, placement into manufactured seeds, and transferring to soil for further growth and development.

Megagametophytes suitable for use in the methods of the disclosure can be from any plant species. In some embodiments, the plant megagametophytes are conifer megagametophytes. Conifer megagametophytes suitable for use in the methods of the disclosure can be from any conifer species including, but not limited to, species within the genera *Pinus, Picea, Tsuga, Pseudotsuga, Thuja, Juniperis, Larix,* and *Sequoia.*

In some embodiments, the conifer megagametophytes are of the family Pinaceae. In some embodiments, the conifer megagametophytes can be Loblolly-pine megagametophytes. In some embodiments, the conifer megagametophytes can be Douglas-fir megagametophytes.

The methods of the present disclosure provide commercial advantages over prior methods of culturing whole megagametophytes. Typically, before cones are collected, embryo development in the megagametophytes is closely monitored, and collection times are established based on maturity of the dominant embryo. In the methods of the present disclosure, embryo maturity does not have to be closely monitored and cones can be harvested before a dominant embryo has formed. Furthermore, fewer megagametophytes will need to be processed to achieve initiation success, which will result in cost savings in labor and materials.

The following examples are provided for the purpose of illustrating, not limiting, the present disclosure.

EXAMPLE 1

In this example, two methods of initiation of embryogenic suspensor mass (ESM) from megagametophytes were compared: 1) culturing intact megagametophytes containing a dominant embryo; and 2) culturing megagametophytes dissected according to the methods of the present disclosure before a dominant embryo has formed. The initiated ESM were further cultured to form developed embryos and germinants.

Cones from three Loblolly pine closed-pollinated crosses were collected and stored at 2-5° C. until seed and megagametophyte removal. Seeds were removed from each group of cones and sterilized according to conventional methods. Megagametophytes were carefully removed intact from the seeds. The megagametophytes were separated into two groups: Group 1: megagametophytes containing a dominant embryo; and Group 2: megagametophytes that did not contain a dominant embryo.

Dissection

Group 1

Megagametophytes containing a dominant embryo were not dissected.

Group 2

Megagametophytes that did not contain a dominant embryo were dissected as follows. A cut at the micropylar end of a megagametophyte was made transverse to the longitudinal axis of the megagametophyte at approximately ¼ of the length of the megagametophyte, as illustrated in FIGS. 1A-1C, to separate the megametophyte into two parts. The early stage embryos were contained in the megagametophyte distal to the micropylar end and were not damaged by the cut.

Placement on Initiation Medium

The megagametophytes from both Group 1 and Group 2 were placed into sterile multiwell plates containing 24 wells of 2 mL of solid initiation medium (Table 2) each such that the ends were in contact with, but not submerged, in the medium. The plates were wrapped and stored at 25° C. in the dark.

After two weeks, 0.20 mL of liquid initiation medium (Table 2 medium, but lacking GELRITE and activated carbon, and containing 10 mg/L abscisic acid) was added to each of the wells in the multiwell plate. Care was taken to pipette the liquid to the side of the multiwell plate and allow it to run down the side of the well onto the gelled medium and not on top of the megagametophyte. The plates were rewrapped and stored at 25° C. in the dark.

Assessment

After a few weeks the multiwell plates were examined for initiation of embryogenic suspensor mass. ESM was observed from the Group 2 dissected megagametophyte after only 3-4 weeks from placement on initiation medium. No ESM was observed from the Group 1 whole megagametophytes; however, zygotic embryos had just begun to extrude from the micropylar end. These extruded embryos multiplied to form ESM after 6-10 weeks from placement on initiation medium.

Initiation Success:

Of the three families of cones, both Group 1 and Group 2 megagametophytes from only two families, Family A and Family B, were studied. Only Group 2 megagametophytes were studied from a third family, Family C. It was found that many of the dominant embryos from Family C had aborted, and therefore whole megagametophytes (Group 1) from Family C were not cultured.

The percentages of ESM formed from Group 1 and Group 2 megagametophytes are shown in Table 1.

TABLE 1

Percentage of Initiation of ESM

|  |  | Family A | Family B | Family C | Mean |
|---|---|---|---|---|---|
| Group 1 | # forming ESM | 493 | 142 | 0 | |
| | # of seeds | 2160 | 1320 | 0 | |
| | Initiation success | 22.8% | 10.8% | 0% | 13.1% |
| Group 2 | # forming ESM | 152 | 92 | 30 | |
| | # of seeds | 192 | 192 | 90 | |
| | Initiation success | 79.1% | 47.9% | 33.3% | 53.4% |

Results

The results in Table 1 illustrate that the dissection method of the present disclosure results in initiation percentages of ESM that are about 3-4 times the initiation percentages of ESM from whole megagamtophytes. Furthermore, the dissection method of the present disclosure resulted in initiation of ESM from megagametophytes that did not contain viable dominant embryos.

Post Initiation Culture

ESM from both Group 1 and Group 2 were further cultured on solid multiplication medium. Four clumps of ESM of 1 cm diameter from each culture were transferred to liquid multiplication medium and then to development medium to form developed cotyledonary embryos.

After the development period, 25 representative viable embryos were selected and transferred to germination medium. At the end of the germination period germination success was assessed. A successful germinant had a root of 1 mm or longer, and at one epicotyl leaf of any length. All of the 25 cultures produced germinants.

Results

The methods of initiation of the present disclosure, in which megagametophytes are dissected before development of the dominant embryo, produced high yields of good quality embryos and successful germination. Early stage dissection of megagametophytes according to the methods of the present disclosure resulted in a higher initiation percentage (mean of 53.1%) as compared to the control whole megagametophytes (mean of 11.2%); and resulted in more rapid proliferation and multiplication of the ESM (4 to 6 weeks for the dissected megagametophyte, compared to 8 to 10 weeks for the control).

EXAMPLE 2

This example provides an exemplary formulation of initiation medium suitable for use in the methods of the present disclosure (Table 2).

TABLE 2

Initiation Medium

Salts (mg/L)

| | |
|---|---|
| NH$_4$NO$_3$ | 200 |
| KNO$_3$ | 909.9 |
| Ca(NO$_3$)$_2$•4H$_2$O | 236.15 |
| MgSO$_4$•7H$_2$O | 246.5 |
| Mg(NO$_3$)$_2$•6H$_2$O | 256.5 |
| MgCl$_2$•6H$_2$O | 101.7 |
| KH$_2$PO4 | 136 |
| CaCl$_2$•2H$_2$O | 50 |
| KI | 4.15 |
| H$_3$BO$_3$ | 15.5 |
| MnSO$_4$•H$_2$O | 10.5 |
| ZnSO$_4$•7H$_2$O | 14.4 |
| Na$_2$MoO$_4$•2H$_2$O | 0.125 |
| CuSO$_4$•5H$_2$O | 0.125 |
| CoCl$_2$•6H$_2$O | 0.125 |
| FeSO4•7H$_2$O | 27.87 |
| Na$_2$EDTA | 37.26 |
| AgNO$_3$ | 3.4 |

Hormones (mg/L)

| | |
|---|---|
| NAA | 2 |
| BAP | 0.63 |
| Kinetin | 0.61 |
| epi-brassinolide | 0.96 |

Vitamins/Amino Acids (mg/L)

| | |
|---|---|
| Nicotinic Acid | 0.5 |
| Pyridoxine HCl | 0.5 |
| Thiamine HCl | 1 |
| Glycine | 2 |
| Biotin | 0.05 |
| Folic Acid | 0.5 |
| Vitamin B-12 | 0.1 |
| Vitamin E | 0.1 |
| α-ketoglutaric acid | 100 |

Sugar/Gelling Agent (mg/L)

| | |
|---|---|
| MES hydrate | 250 |
| Myo-Inositol | 20000 |
| Casein hydrolysate | 500 |
| L-glutamine | 450 |
| Maltose | 15000 |
| GELRITE | 2000 |
| Activated carbon | 50 |

EXAMPLE 3

In this example, two methods of initiation of embryogenic suspensor mass (ESM) from megagametophytes were compared: 1) culturing intact megagametophytes containing a dominant embryo; and 2) culturing megagametophytes dissected according to the methods of the present disclosure before a dominant embryo has formed.

Group 1 megagametophytes contained a dominant embryo and were not dissected. Group 2 megagametophytes did not contain a dominant embryo and were dissected as described in Example 1. Group 1 and Group 2 megagametophytes were cultured on initiation medium as described in Example 1. The initiated ESM were further cultured on capture medium.

Results

The percentage of ESM from each Group that were transferred to capture medium was compared. The data is provided in Table 3.

TABLE 3

| Group | Mean | Test at $\alpha = 0.10$ | L90 | U90 |
|---|---|---|---|---|
| 1 | 0.193 | B | 0.180 | 0.207 |
| 2 | 0.725 | A | 0.682 | 0.764 |

Table 3 provides the estimated means of the percentage of ESM from each group transferred to capture medium and comparison between the percentages of Group 1 and Group 2. L90 and U90 are the lower and upper 90% confidence limits, respectively, for each mean. The column "Test at $\alpha=0.10$" summarizes test results comparing combined means. Means with different symbols are statistically different at $\alpha=0.10$.

The percentage of ESM initiated from megagametophytes dissected according to the methods of the present disclosure (Group 2) and transferred to capture medium was 72.5%. The percentage of ESM initiated from whole megagametophytes (Group 1) and transferred to capture medium was only 19.3%.

The data in Table 3 illustrates that the percentage of ESM initiated from megagametophytes dissected according to the methods of the present disclosure was statistically significantly greater (p-value <0.0001) than the percentage of ESM initiated from whole megagametophytes.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of initiating a plurality of plant somatic embryos from a megagametophyte comprising the steps of:
    (a) dissecting a megagametophyte transversally to the longitudinal axis into two parts at a position that is located proximal to the micropylar end, wherein the megagametophyte is dissected transversally to the longitudinal axis at a position that is from about one-eighth to about one-half the length of the megagametophyte and proximal to the micropylar end; and
    (b) culturing either or both parts of the dissected megagametophyte to initiate the formation of embryogenic suspensor mass,
wherein the megagametophyte is dissected before a dominant embryo has formed in the megagametophyte.

2. The method of claim 1, wherein the megagametophyte is dissected transversally to the longitudinal axis at a position that is about one-eighth the length of the megagametophyte and proximal to the micropylar end.

3. The method of claim 1, wherein the megagametophyte is dissected transversally to the longitudinal axis at a position that is about one-fourth the length of the megagametophyte and proximal to the micropylar end.

4. The method of claim 1, wherein the megagametophyte is dissected transversally to the longitudinal axis at a position that is about one-half the length of the megagametophyte and proximal to the micropylar end.

5. The method of claim 1, wherein either or both parts of the dissected megagametophyte are cultured on initiation medium for a period of time sufficient to form an embryogenic suspensor mass.

6. The method of claim 5, wherein either or both parts of the dissected megagametophyte are cultured on initiation medium for a period of about three to twelve weeks to form an embryogenic suspensor mass.

7. The method of claim 6, wherein either or both parts of the dissected megagametophyte are cultured on initiation medium for a period of about three to four weeks to form an embryogenic suspensor mass.

8. The method of claim 5, further comprising culturing the embryogenic suspensor mass to multiply the embryogenic suspensor mass.

9. The method of claim 8, further comprising culturing the multiplied embryogenic suspensor mass to form cotyledonary embryos.

10. The method of claim 9, further comprising culturing the cotyledonary embryos to form germinants.

11. The method of claim 1, wherein the plurality of plant somatic embryos are conifer somatic embryos.

12. The method of claim 11, wherein the plurality of conifer somatic embryos are somatic embryos of the family Pinaceae.

13. The method of claim 12, wherein the plurality of conifer somatic embryos are Loblolly-pine somatic embryos.

14. The method of claim 11, wherein the plurality of conifer somatic embryos are Douglas-fir somatic embryos.

\* \* \* \* \*